United States Patent
Chung (10) Patent No.: US 11,117,953 B2
(45) Date of Patent: *Sep. 14, 2021

(54) MICROORGANISM FOR DELIVERING DRUG FOR TREATMENT OF GASTROINTESTINAL DISEASE, WHICH EXPRESSES AND SECRETES CYSTATIN, AND PHARMACEUTICAL COMPOSITION FOR PREVENTING OR TREATING GASTROINTESTINAL DISEASE, WHICH INCLUDES THE SAME

(71) Applicant: CELL BIOTECH CO., LTD., Gimpo-si (KR)

(72) Inventor: Myung Jun Chung, Seoul (KR)

(73) Assignee: Cell Biotech Co., Ltd., Gyeonggi-do (KR)

( * ) Notice: Subject to any disclaimer, the term of this patent is extended or adjusted under 35 U.S.C. 154(b) by 203 days.

This patent is subject to a terminal disclaimer.

(21) Appl. No.: 16/471,912

(22) PCT Filed: Oct. 16, 2018

(86) PCT No.: PCT/KR2018/012159
§ 371 (c)(1),
(2) Date: Jun. 20, 2019

(87) PCT Pub. No.: WO2019/139228
PCT Pub. Date: Jul. 18, 2019

(65) Prior Publication Data
US 2019/0330312 A1    Oct. 31, 2019

(30) Foreign Application Priority Data
Jan. 9, 2018 (KR) .................... 10-2018-0003005

(51) Int. Cl.
*C07K 14/81* (2006.01)
*A61K 35/747* (2015.01)
(Continued)

(52) U.S. Cl.
CPC ........ *C07K 14/8139* (2013.01); *A61K 35/747* (2013.01); *A61K 38/1722* (2013.01);
(Continued)

(58) Field of Classification Search
None
See application file for complete search history.

(56) References Cited

U.S. PATENT DOCUMENTS

2002/0137140 A1    9/2002  Vrang et al.
2019/0328800 A1*  10/2019  Chung .................... C12R 1/245

FOREIGN PATENT DOCUMENTS

JP    2004-511248 A    4/2004
KR    2010-0003490 A   1/2010
(Continued)

OTHER PUBLICATIONS

Cano-Garrido, O. et al., "Lactic acid bacteria: reviewing the potential of a promising delivery live vector for biomedical purposes", Microbial Cell Factories, 2015, vol. 14, 137, pp. 1-12.
(Continued)

*Primary Examiner* — David W Berke-Schlessel
(74) *Attorney, Agent, or Firm* — Hamre, Schumann, Mueller & Larson, P.C.

(57) ABSTRACT

The present invention relates to a microorganism for drug delivery, which has been transformed with a gene construct including a therapeutically active peptide, is delivered safely into the intestines through oral administration, and expresses and secretes a cystatin in the gastrointestinal tract, and also relates to a pharmaceutical composition for prevention or treatment of gastrointestinal disease, which includes the
(Continued)

same. The present invention demonstrates the safety and superiority of lactic acid bacteria as a system for delivering a protein-based drug, and thus it is expected the lactic acid bacteria will be widely used as an agent for treatment of gastrointestinal disease in the medical field.

4 Claims, 4 Drawing Sheets

Specification includes a Sequence Listing.

(51) Int. Cl.
| | |
|---|---|
| *A61K 38/17* | (2006.01) |
| *C12P 21/02* | (2006.01) |
| *C12N 1/20* | (2006.01) |
| *C12R 1/23* | (2006.01) |
| *C12R 1/24* | (2006.01) |
| *C12R 1/25* | (2006.01) |

(52) U.S. Cl.
CPC .............. *C12N 1/205* (2021.05); *C12P 21/02* (2013.01); *C12R 2001/23* (2021.05); *C12R 2001/24* (2021.05); *C12R 2001/25* (2021.05)

(56) References Cited

FOREIGN PATENT DOCUMENTS

| KR | 10-1791876 B1 | 10/2017 |
|---|---|---|
| WO | 2008/015014 A2 | 2/2008 |
| WO | 2014/037505 A1 | 3/2014 |

OTHER PUBLICATIONS

Fichera, G. A. and Giese, G., "Non-immunologically-mediated cytotoxicity of Lactobacillus casei and its derivative peptidoglycan against tumor cell lines", Cancer Lett., 85, 1994, pp. 93-103.
International Search Report and Written Opinion issued for International Application No. PCT/KR2018/012159, dated Feb. 1, 2019, 12 pages.

* cited by examiner

SEQUENCE LISTING

```
<160> NUMBER OF SEQ ID NOS: 6

<210> SEQ ID NO 1
<211> LENGTH: 324
<212> TYPE: DNA
<213> ORGANISM: Artificial Sequence
<220> FEATURE:
<223> OTHER INFORMATION: Primer ChoS

<400> SEQUENCE: 1
ggatccgtga tgtacgtaag aaagatttac gtcaaatcac aacggccgta ggtgacggtg      60
gcgtcgctgg acaacaagcg tatgaatata ttcaagcttt aaatgattaa agtcaaaata     120
agccacggtg aaaaccgggg cttttctttt tgccaaaatt caaaaagtga ttggtctata     180
cctaaaatta aaaaaacgct ttctggtatt ccatgggtat tgtataatga aagtaactat     240
aagttacatc ataggaggac ttttgaatga aaaaaaagat tatctcagct attttaatgt     300
ctacagtgat actttctgct gcag                                            324

<210> SEQ ID NO 2
<211> LENGTH: 324
<212> TYPE: DNA
<213> ORGANISM: Artificial Sequence
<220> FEATURE:
<223> OTHER INFORMATION: Primer PK

<400> SEQUENCE: 2
ggatccctaa agatcgcgtt ttagcaagta agatgggtgc ttacgctgtt gagctactcc      60
ttgaaggtaa gggtggttta gcagttggaa tcttagaaaa taaggttcaa gctcataaca     120
tgcttgactt gtttgatgca aaacatcaag cagatgattc actttaccaa ttaagtgaag     180
atttatcatt ctagagttct attaatattt ggataaaatg acttaagaag tctttttataa    240 tttaaaatca agggagagat tctgtaatga aaaaaaagat tatctcagct attttaatgt     300
ctacagtgat actttctgct gcag                                            324

<210> SEQ ID NO 3
<211> LENGTH: 324
<212> TYPE: DNA
<213> ORGANISM: Artificial Sequence
<220> FEATURE:
<223> OTHER INFORMATION: Primer GK

<400> SEQUENCE: 3
ggatccataa tctggtaaat tagttgagat ggtattatga aaacacttta tgatgtgcaa      60
caacttttaa agcaattcgg aatatttgtt tacgttggaa aacgtaaatg ggatattgaa     120
ttgatgagta ttgaattgaa aaatttgtac aaagcaggag tcgtcgataa accgacttat     180
```

```
gttaaagctc agttggtttt acgacatgag catcatattg aagaggttag agataaccaa    240
caaaaataat ggagggtttc gaagtaatga aaaaaaagat tatctcagct attttaatgt    300
ctacagtgat actttctgct gcag                                          324
```

```
<210> SEQ ID NO 4
<211> LENGTH: 324
<212> TYPE: DNA
<213> ORGANISM: Artificial Sequence
<220> FEATURE:
<223> OTHER INFORMATION: Primer G6Pi

<400> SEQUENCE: 4
ggatccatgc cggctaaagt ggtggataaa ttgaatcatc cccaagaact ggaataagat    60
aaaattgtag tgcttttcagg ctttaccagc catcttttga aaaattaat ttctttcaaa    120 agtgcgtgtg acaggtgatc aactagatta aatggggagg gtatcccagt aaatattagg    180
ttaaatcgga taggcttaac caaattaagt aattttattg taatggta cagataaaga    240 attttaaaca aaaggggtag ttattaatga aaaaaaagat tatctcagct attttaatgt    300
ctacagtgat actttctgct gcag                                          324
```

```
<210> SEQ ID NO 5
<211> LENGTH: 324
<212> TYPE: DNA
<213> ORGANISM: Artificial Sequence
<220> FEATURE:
<223> OTHER INFORMATION: Primer L-LDH

<400> SEQUENCE: 5
ggatcctcat ttcatgttta tttttccacc ctcaacacgc aaaaacggct gaaagagcaa    60 aaaccccctca gctgtccacg tttatttca tgtaatatta ccatattatt gaccccaagc    120
gggtctttta acctctaact tatcaatcac tttactaact atacccgaac ttcataaaat    180
ttttactcaa ctttcttta tgaaaatgct atacttagta ttgtttgata aattcaaata    240
ttatatgaaa aaggggatt gatcttatga aaaaaaagat tatctcagct attttaatgt    300
ctacagtgat actttctgct gcag                                          324
```

```
<210> SEQ ID NO 6
<211> LENGTH: 4757
<212> TYPE: DNA
<213> ORGANISM: Artificial Sequence
<220> FEATURE:
<223> OTHER INFORMATION: Plasmid pCBT24-2

<400> SEQUENCE: 6
aagttaatgt aagccttaag gtttcaacta aagcaattac ggtcaaccat aaccatagta    60
ttggattgtc attttattgg ctataaaata gtaaatcagt gaatttcatt ggatccgcta    120
aagatcgcgt tttagcaagt aagatgggtg cttacgctgt tgagctactc cttgaaggta    180
agggtggttt agcagttgga atcttagaaa ataaggttca agctcataac atgcttgact    240
tgtttgatgc aaaacatcaa gcagatgatt cactttacca attaagtgaa gatttatcat    300
tctagagttc tattaatatt tggataaaat gacttaagaa gtcttttata atttaaaatc    360
aagggagaga ttctgtaatg aaaaaaaaga ttatctcagc tattttaatg tctacagtga    420
tactttctgc tgcagcccg ttgtcaggtg tttacgctga gtaattatt atggctaccg    480 ttgatccaga aaagactcta ttccttgatg aaccaatgaa taagttttt gattggtcta    540 acagtgaggc tccggtgcga gatgccttat gggattacta tatggaaaag aatagccgtg    600
```

```
acacgatcaa aacagaagaa gaaatgaaac ctgtattaga tatgtcagat gacgaagtta    660
aagcattagc ggagaaagtc ttgaaaaagt aacctgacaa gaaccagtct gctattgata    720 gactatttt gtccgtgaaa tcctcgcgta tttccgtgag gagcatagta tatttagcga    780
tcttcaaatt ttaagtatat tgattcatat gtttatcctc ctaagtttga ggacaaatcg    840
gattccacgg cctcaatgac tgagctccgc ctatttttat aggttaatgt catgataata    900
atggtttctt agcgattcac aaaaaatagg cacacgaaaa acaagttaag ggatgcagtt    960
tatgcatccc ttaacttact tattaaataa tttatagcta ttgaaaagag ataagaattg   1020
ttcaaagcta atattgttta aatcgtcaat tcctgcatgt tttaaggaat tgttaaattg   1080
attttttgta aatatttct tgtattcttt gttaacccat ttcataacga ataattata    1140 cttttgttta tctttgtgtg atattcttga ttttttcta cttaatctga taagtgagct   1200
attcacttta ggtttaggat gaaatattc tcttggaacc atacttaata tagaaatatc   1260
aacttctgcc attaaaagta atgccaatga gcgttttgta tttaataatc ttttagcaaa   1320
cccgtattcc acgattaaat aaatctcatt agctatacta tcaaaacaa ttttgcgtat    1380 tatatccgta cttatgttat aaggtatatt accatatatt ttataggatt ggttttagg    1440 aaatttaaac tgcaatatat ccttgtttaa aacttggaaa ttatcgtgat caacaagttt   1500
attttctgta gttttgcata atttatggtc tatttcaatg gcagttacga aattacacct   1560
ctttactaat tcaagggtaa aatggccttt tcctgagccg atttcaaaga tattatcatg   1620
ttcatttaat cttatatttg tcattatttt atctatatta tgttttgaag taataaagtt   1680
ttgactgtgt tttatatttt tctcgttcat tataaccctc tttaatttgg ttatatgaat   1740
tttgcttatt aacgattcat tataaccact tattttttgt ttggttgata atgaactgtg   1800
ctgattacaa ttaattaaaa atactaaaaa tgcccatatt ttttcctcct tataaaatta   1860
gtataattat agcacgaaaa ggatctaggt gaagatcctt tttgataatc tcatgaccaa   1920
aatcccttaa cgtgagtttt cgttccactg agcgtcagac cccgtagaaa agatcaaagg   1980
atcttcttga gatccttttt ttctgcgcgt aatctgctgc ttgcaaacaa aaaaaccacc   2040
gctaccagcg gtggtttgtt tgccggatca agagctacca actcttttc cgaaggtaac   2100 tggcttcagc agagcgcaga taccaaatac tgttcttcta gtgtagccgt agttaggcca   2160
ccacttcaag aactctgtag caccgcctac atacctcgct ctgctaatcc tgttaccagt   2220
ggctgctgcc agtggcgata agtcgtgtct taccgggttg gactcaagac gatagttacc   2280
ggataaggcg cagcggtcgg gctgaacggg gggttcgtgc acacagccca gcttggagcg   2340
aacgacctac accgaactga gatacctaca gcgtgagcta tgagaaagcg ccacgcttcc   2400
cgaagggaga aaggcggaca ggtatccggt aagcggcagg gtcggaacag gagagcgcac   2460
gagggagctt ccagggggaa acgcctggta tctttatagt cctgtcgggt ttcgccacct   2520
ctgacttgag cgtcgatttt tgtgatgctc gtcagggggg cggagcctat ggaaaaacgc   2580
cagcaacgcg gccttttac ggttcctggc cttttgctgg cctttgctc acatgttctt    2640 tcctgcgtta tcccctgatt ctgtggataa ccgtattacc gcctttgagt gagctgatac   2700
cgctcgccgc agccgaacga ccgagcgcag cgagtcagtg agcgaggaaa tcgatactga   2760
attggcgaaa gccaaagttt ctataaaacc ttgctttcct gcttaacggc gagtgaaaaa   2820
gcggttaagc tggctcagct tggacggggt cggggcgtt agcgtccgta ttaaatgtgg   2880
cttaccataa ccaacgaaca gagtgaggtg caaggagctg tgcgactgga gtttaatgtg   2940
```

-continued

```
agccggtttt tggctcactc ctttgtgttt tttgtttcta gattttaatc tcgtacagcg    3000
gtgcctcttt tatacctctt ttataaacct cttttaaacc tcttttagac ccctcttgag    3060
ccttactctc ccaaggctca cagaaggtta tcaagtacct tttgtctgtt tatcaagtac    3120
cttttgtctg tttatcaagt accttttgtc tgtttatcaa gtaccttttg tctgtttatc    3180 aagtacctt ataagttctg tacttgataa aaaggtactt ttattttaat atgtgtttga     3240
ggtgataatc atggctaatg agttagttaa gtatgatcct gagttgaata ctattccctt    3300
gagaaaattt accccaattg agatgaattt attttttttca attatttccc gcatgcggga   3360
tcaagggaat aaaactgttc gtttctcttt tgaccagtta aaagagctta gtaactataa    3420
accaaccgca aataaacgtt ttattgatga tattgaaaat acataccaaa agatcctcag    3480
ccttaggttt ggccgtagaa gtaagagtgg cttaaatcgt gaatttttttg ttatgtttac   3540 tgaatttgaa attaaaggtg aagctgaaga accttatgtt gatattcaga tttatcccaa    3600
agcattgcac ttgctaaacg atttagaaag ttgggttcgt tatgccctaa cagaatttag    3660
aaatttaaaa agcagttacg ctaaaacaat gtttcgtcta attaagcaat ttcgaactac    3720
tggctattct tatttctcta aagaagattt ttttgaattg cttgatatac ctaaaagtta    3780
ttggaatagt ccttcaaagg ttgacaaaaa ggttattaag ccaattagag aagaattaac    3840
cccgcttttt agagggctaa cgattagaaa aaaatatggt aaaggcagag gaaaaccagt    3900
tatcggttat tcttttactt ggaaacctga agcaaggac gcaaatgatt tttctcaagg     3960
caaatttcaa gatgagcgtc aaaaactctt taacattcag cacaatgatg aattatcaga    4020
taaagaaaag tggcgtgcaa ttgacaaagt taaatgcttg cctttaggaa caactgaaaa    4080
acaggtactg gctgaaaaac aagctgaaca tgatcaaaaa atcagagatc aagcaagaca    4140
agaatttctc gctgatctcc gaaagggggtt ttaaaatcat gtctaaaact attagagaac   4200
ttgctgatga attgaatgtc tccaaacaga ctattcaata tcactaccaa agactaccag    4260
caaagaacca acaaaagaat agtcagggca caaaccttat tagtcctaca gcagaaagaa    4320
ttataagaag caaggtagca aagcctttgc tagcaaaaaa acagcaaaga ggtagcaaag    4380
aattgccaaa gactagcaaa gaaaataatg atctggttgc tactctgaga agagaagtag    4440
aagatttaaa ggctcaacgt gacaaacagc ttgctaccaa agaccgacaa atagaccatc    4500
taacaaaatt ggtggatcag cagcaacaat tacaattagc aacagtagca gataaccgtc    4560
gattaaaaga tcatgtacaa aagctaagtg ggcaactaac tcaaaaaact aacgacaact    4620
tgtcgaccgg aaatgatctt tttaacatcc aagataaaga aagcaaaata gctaaacaga    4680
agattgttaa atctggtagt aataaagatg gcatacacac aaatagagct attaaacgtt    4740
ggtggaaatt ctggtaa                                                   4757
```

MICROORGANISM FOR DELIVERING DRUG FOR TREATMENT OF GASTROINTESTINAL DISEASE, WHICH EXPRESSES AND SECRETES CYSTATIN, AND PHARMACEUTICAL COMPOSITION FOR PREVENTING OR TREATING GASTROINTESTINAL DISEASE, WHICH INCLUDES THE SAME

STATEMENT AS TO GOVERNMENT-FUNDED RESEARCH

This invention was made with Korean Government support under a grant No. 52367890 funded by the Ministry of Trade, Industry and Energy, under the supervision of the Republic of Korea Small and Medium Business Administration, from the WC300 project for developing drug-delivery probiotics for treatment of inveterate intestinal disease, study period was 2016 Feb. 1-2020 Dec. 31.

TECHNICAL FIELD

The present invention relates to a microorganism for delivering a drug for treating gastrointestinal disease, which expresses and secretes a cystatin, and a composition for preventing or treating gastrointestinal disease, which includes the same, and more specifically to a microorganism for gastrointestinal delivery of a polypeptide for treating gastrointestinal disease, and a pharmaceutical composition for preventing or treating gastrointestinal disease, including the same.

BACKGROUND ART

Lactic acid bacteria are microorganisms widely distributed in nature, and produce lactic acid by anaerobic fermentation of carbohydrates. Due to their advantage of being non-pathogenic bacteria, lactic acid bacteria have recently been widely used in industrial fields as well as in medical fields. These lactic acid bacteria are known to play an important role in maintaining gastrointestinal health, and it has been reported that health can be improved by taking lactic acid bacteria. For example, since it was reported that lactic acid bacteria can inhibit tumors in the large intestine, the importance of lactic acid bacteria in the treatment of chronic diseases related to eating habits, such as cancer, has been highlighted.

Animal experiments and the like have demonstrated that the anticancer effects of lactic acid bacteria are attributable to the inhibition of production of carcinogenic substances by improvement of intestinal microbiota and to the inhibition of cancer cell proliferation by the activation of intestinal immune functions.

Meanwhile, it has been reported that lactic acid bacteria exhibit anticancer effects by promoting the immunity of host cells and also have a cytotoxic effect directly on cancer cells, and these activities are attributed mainly to peptidoglycans (Fichera, G. A., and Giese, G., Cancer Lett., 85:93-103, 1994).

Research into lactic acid bacteria has accelerated based on research results accumulated so far, and research on high value-added products using lactic acid bacteria has been actively conducted in earnest. In recent years, interest in lactic acid bacteria as live mucosal vaccine vectors has increased. However, to produce foreign proteins by lactic acid bacteria, effective and stable expression system were required in the lactic acid bacteria. Although there have been research reports that several foreign proteins were expressed in lactic acid bacteria, their expression levels are too low to be used industrially yet.

DISCLOSURE

Technical Problem

The present invention has been conceived to overcome the above-described conventional drawbacks, and an object of the present invention is to provide a microorganism for delivering a cystatin effective against gastrointestinal disease to a specific site in the gastrointestinal tract, wherein the microorganism has been transformed with a gene encoding the cystatin and is capable of acting as a drug delivery system.

Another object of the present invention is to provide a pharmaceutical composition for preventing or treating gastrointestinal disease, which includes a microorganism as a drug delivery system which is used to deliver a cystatin beneficial for treatment of gastrointestinal disease to a specific site in the gastrointestinal tract and which is capable of expressing and secreting a therapeutically effective high level of biologically active polypeptide at a predetermined location in the gastrointestinal tract.

Technical Solution

One aspect of the present invention to achieve the above-described objects is directed to a microorganism for delivering a drug for treatment of gastrointestinal disease, wherein the microorganism has been transformed with a gene construct, including a polynucleotide encoding a cystatin or active fragment of the cystatin operably linked to an exogenous promoter and a gene encoding a secretion signal peptide, and expresses and secretes the cystatin in the gastrointestinal tract.

The exogenous promoter is at least one promoter selected from the group consisting of SEQ ID NO: 1 (Chos promoter), SEQ ID NO: 2 (PK promoter), SEQ ID NO: 3 (GK promoter), SEQ ID NO: 4 (G6Pi promoter), SEQ ID NO: 5 (L-LDH promoter), and combinations thereof, derived from *Pediococcus pentosaceus*.

The strain may belong to the genus *Lactobacillus, Latococcus, Leuconostoc, Pediococcus*, or *Bifidobacterium*.

Specific examples of the strain include *Lactobacillus rhamnosus, Lactobacillus acidophilus, Lactobacillus paracasei, Lactobacillus plantarum, Pediococcus pentosaceus*, or *Lactobacillus brevis* strains. Preferably, the strain may be a *Pediococcus pentosaceus* strain.

The secretion signal peptide is a USP45 secretion signal peptide, Usp45 N4, or a *Lactobacillus brevis* S-layer protein signal peptide.

The cystatin is selected from the group consisting of cystatin A, cystatin B, cystatin C, cystatin D, cystatin S, egg white cystatin, milk cystatin, and kininogen.

The gene construct transformed into the microbial strain as a drug delivery system may further include, downstream of the promoter, a second promoter, a second secretion signal peptide, and a second heterologous nucleic acid sequence, and the second promoter may be the same as or different from the first promoter.

The strain of the present invention may be used for prevention or treatment of gastrointestinal diseases, such as colorectal cancer, colon polyps, colitis, ischemic gastrointestinal diseases, dysentery, intestinal vascular dysplasia, diverticulosis, irritable bowel syndrome, and Crohn's disease.

Another aspect of the present invention to achieve the above-described objects is directed to a pharmaceutical composition for prevention or treatment of gastrointestinal disease, which includes a strain that produces a cystatin or an active fragment of the cystatin.

Still another aspect of the present invention to achieve the above-described objects is directed to a pharmaceutical composition for prevention or treatment of gastrointestinal disease, including a *Pediococcus pentosaceus* strain, wherein the *Pediococcus pentosaceus* strain includes a heterologous nucleic acid encoding a therapeutic peptide having a therapeutic effect against at least one gastrointestinal disease, and the heterologous nucleic acid includes at least one promoter operably linked to the heterologous nucleic acid and selected from SEQ ID NOs: 1 to and combinations thereof, derived from *Pediococcus pentosaceus*; and a gene encoding a secretion signal peptide.

Advantageous Effects

A microbial strain for drug delivery, which includes a promoter isolated from the glycolysis pathway of lactic acid bacteria according to the present invention, is capable of effectively functioning as a drug delivery system by continuously expressing and secreting a high level of therapeutically active peptide while residing in the intestines.

Furthermore, the microorganism of the present invention is obtained by transforming lactic acid bacteria with a gene construct encoding a human natural protein confirmed to inhibit the growth and metastasis of cancer cells, and thus can maximize therapeutic effects without side effects.

The pharmaceutical composition of the present invention is a safe substance which not only exhibits an excellent inhibitory effect against the growth of colorectal cancer cells, but is also not toxic to normal cells, indicating that it may advantageously be used for the prevention and treatment of colorectal cancer.

According to the present invention, a therapeutic peptide synthesized in situ by the recombinant microorganism can be delivered locally by an oral route, and thus the dose and treatment timing necessary for treatment can be precisely controlled, thereby eliminating the need for systemic administration.

The present invention may advantageously be used for the local delivery of a substance which is unstable or difficult to produce in large amounts. According to the present invention, it is possible to continuously and locally deliver a therapeutic peptide at higher concentrations than those obtained by systemic delivery without side-effect problems.

MODE FOR INVENTION

The present invention will be described in more detail below with reference to the accompanying drawings.

Unless otherwise defined, all the scientific and technical terms used in the specification have the same meanings as commonly understood by those skilled in the technical field to which the present invention.

The term "nucleic acid" refers to a deoxyribonucleotide or ribonucleotide polymer in either single- or double-stranded form, and, unless otherwise limited, encompasses known analogs of natural nucleotides that that hybridize to nucleic acids in a manner similar to naturally occurring nucleotides. Unless otherwise indicated, a particular nucleic acid sequence includes its complementary sequence.

As used herein, the term "promoter" refers to a DNA sequence capable of controlling the expression of a coding sequence or functional RNA. Any person skilled in the art will easily recognize a promoter region. The promoter consists of proximal and more distal upstream elements. Proximal elements include a TATA box capable of directing RNA polymerase II to initiate RNA synthesis at an appropriate transcription initiation site.

The term "biologically active molecule (BAM)" refers to substances which are involved in gene therapy or capable of regulating immune responses, and include substances capable of regulating intracellular signal transduction mechanisms or the expression of other particular genes. These substances may include growth factors, substances for cancer treatment, tumor suppressors, cytokines, interferons, and the like.

As used herein, a "heterologous sequence" or a heterologous nucleic acid" means one that originates from a foreign source (or species) or, if originates from the same source, is modified from its original form. Thus, a heterologous nucleic acid operably linked to a promoter is derived from a source different from that from which the promoter was derived, or, if derived from the same source, is modified from its original form.

The term "operably linked" refers to functional linkage between a nucleic acid expression control sequence (such as a promoter, signal sequence, or array of transcription factor binding sites) and a heterologous nucleic acid sequence, wherein the expression control sequence affects transcription and/or translation of the nucleic acid corresponding to the heterologous nucleic acid sequence.

As used herein, the terms "protein" and "polypeptide" are used interchangeably. A "polypeptide" refers to a polymer of amino acids, and does not refer to a specific length of the molecule. This term also includes post-translational modifications of the polypeptide, such as glycosylation, phosphorylation and acetylation.

As used herein, the term "prevention" means a medical or public health procedure whose purpose is to prevent disease rather than to treat or cure disease.

As used herein, the term "treatment" means a medical or public health procedure whose purpose is to treat or cure disease.

As used herein, the term "therapeutically effective amount" refers to the amount of therapeutic substance or composition effective to treat a disease or disorder in a subject, e.g., human or animal, i.e., to obtain a desired local or systemic effect and performance.

As used herein, the term "pharmaceutically acceptable" means compatible with the other ingredients of a pharmaceutical composition and not deleterious to the recipient thereof.

One aspect of the present invention to achieve the above-described objects is directed to a microorganism for delivering a drug for treatment of gastrointestinal disease, wherein the microorganism has been transformed with a gene construct, including a polynucleotide encoding a cystatin or active fragment of the cystatin operably linked to an exogenous promoter and a gene encoding a secretion signal peptide, and expresses and secretes the cystatin in the gastrointestinal tract.

The microorganism of the present invention may be used as a medicament. Although this medicament may be administered alone as a therapeutic agent, it is preferably provided as a pharmaceutical formulation prepared by mixing with one or more pharmacologically acceptable carriers by any method known in the technical field of pharmaceutics.

Cystatins are substances that inhibit the activity of intracellular proteases, and belong to a large superfamily of proteins, many of which inhibit cysteine proteases of the C1 class (cathepsins). Virtually all organisms produce one or more members of the cystatin superfamily. Basically, there are three major cystatin families, the types I, II, and III cystatins and a number of cystatin-related protein families. The cystatins may be classified into family I (cystatin A, and cystatin B), secretory family II (cystatin C, cystatin D, cystatin S, egg white cystatin, and milk cystatin), and family III (kininogens). The cystatins function as strong inhibitors of various cancers, and also the cystatins inhibit the activity of protein kinase C (PKC), a critical enzyme which helps drive the metastatic propensity of many cancer types.

In one example, the cystatin A protein preferably has the amino acid sequence as set forth in Table 1 below, but is not necessarily limited thereto.

TABLE 1

| Definition | Sequence |
|---|---|
| Nucleotide sequence of cystatin A protein | MIPGGLSEAKPATPEIQEIVDKVKPQLEEKTNETYGKLEAVQYKTQVVAGTNYYI KVRAGDNKYMHLKVFKSLPGQNEDLVLTGYQVDKNKDDELTGF |
| Nucleotide sequence of the gene encoding cystatin A protein | ATGATTCCAGGTGGTCTTTCAGAAGCTAAACCAGCTACACCAGAAATTCAAGAAA TTGTTGATAAAGTTAAACCACAACTTGAAGAAAAACAAACGAAACATACGGTAA ACTTGAAGCTGTTCAATACAAAACACAAGTTGTTGCTGGTACAAACTACTACATT AAAGTTCGTGCTGGTGATAACAAATACATGCATCTTAAAGTTTTTAAATCACTTC CAGGTCAAAACGAAGATCTTGTTCTTACAGGTTACCAAGTTGATAAAAACAAAGA TGATGAACTTACAGGTTTTTAGC |

In the present invention, five strong promoters for expression of a target protein in lactic acid bacteria were selected. The exogenous promoter may be selected from SEQ ID NO: 1 (Chos promoter, L-carnitine, choline ABC transporter), SEQ ID NO: 2 (PK promoter, pyruvate kinase), SEQ ID NO: 3 (GK promoter, glucokinase), SEQ ID NO: 4 (G6Pi promoter, glucose 6-phosphate isomerase), SEQ ID NO: 5 (L-LDH promoter, L-lactate dehydrogenase), and combinations thereof, derived from *Pediococcus pentosaceus*.

TABLE 2

| Abbreviation of primer name | Sequence (5' → 3') |
|---|---|
| ChoS | GGATCCGTGATGTACGTAAGAAAGATTTACGTCAAATCACAACGGCCGTAGGTGACGGTG GCGTCGCTGGACAACAAGCGTATGAATATATTCAAGCTTTAAATGATTAAAGTCAAAATA AGCCACGGTGAAAACCGGGGCTTTTCTTTTTGCCAAAATTCAAAAAGTGATTGGTCTATA CCTAAAATTAAAAAAACGCTTTCTGGTATTCCATGGGTATTGTATAATGAAAGTAACTAT AAGTTACATCATAGGAGGACTTTTGAATGAAAAAAAAGATTATCTCAGCTATTTTAATGT CTACAGTGATACTTTCTGCTGCAG |
| PK | GGATCCCTAAAGATCGCGTTTTAGCAAGTAAGATGGGTGCTTACGCTGTTGAGCTACTCC TTGAAGGTAAGGGTGGTTTAGCAGTTGGAATCTTAGAAAATAAGGTTCAAGCTCATAACA TGCTTGACTTGTTTGATGCAAAACATCAAGCAGATGATTCACTTTACCAATTAAGTGAAG ATTTATCATTCTAGAGTTCTATTAATATTTGGATAAAATGACTTAAGAAGTCTTTTATAA TTTAAAATCAAGGGAGAGATTCTGTAATGAAAAAAAAGATTATCTCAGCTATTTTAATGT CTACAGTGATACTTTCTGCTGCAG |
| GK | GGATCCATAATCTGGTAAATTAGTTGAGATGGTATTATGAAAACACTTTATGATGTGCAA CAACTTTTAAAGCAATTCGGAATATTTGTTTACGTTGGAAAACGTAAATGGGATATTGAA TTGATGAGTATTGAATTGAAAAATTTGTACAAAGCAGGAGTCGTCGATAAACCGACTTAT GTTAAAGCTCAGTTGGTTTTACGACATGAGCATCATATTGAAGAGGTTAGAGATAACCAA CAAAAATAATGAGGGTTTCGAAGTAATGAAAAAAAAGATTATCTCAGCTATTTTAATGT CTACAGTGATACTTTCTGCTGCAG |

TABLE 2-continued

| Abbreviation of primer name | Sequence (5' → 3') |
|---|---|
| G6Pi | GGATCCATGCCGGCTAAAGTGGTGGATAAATTGAATCATCCCCAAGAACTGGAATAAGAT<br>AAAATTGTAGTGCTTTCAGGCTTTACCAGCCATCTTTTGAAAAAATTAATTTCTTTCAAA<br>AGTGCGTGTGACAGGTGATCAACTAGATTAAATGGGGAGGGTATCCCAGTAAATATTAGG<br>TTAAATCGGATAGGCTTAACCAAATTAAGTAATTTTATTGTATAATGGTACAGATAAAGA<br>ATTTTAAACAAAAGGGGTAGTTATTAATGAAAAAAAAGATTATCTCAGCTATTTTAATGT<br>CTACAGTGATACTTTCTGCTGCAG |
| L-LDH | GGATCCTCATTTTCATGTTATTTTTCCACCCTCAACACGCAAAAACGGCTGAAAGAGCAA<br>AAACCCCTCAGCTGTCCACGTTTATTTTTCATGTAATATTACCATATTATTGACCCCAAGC<br>GGGTCTTTTAACCTCTAACTTATCAATCACTTTACTAACTATACCCGAACTTCATAAAAT<br>TTTTACTCAACTTTCTTTTATGAAAATGCTATACTTAGTATTGTTTGATAAATTCAAATA<br>TTATATGAAAAAGGGGATTGATCTTATGAAAAAAAAGATTATCTCAGCTATTTTAATGT<br>CTACAGTGATACTTTCTGCTGCAG |

The gene construct includes a promoter which, when introduced into microbial cells, promotes the expression of a heterologous nucleic acid encoding a biologically active foreign protein. Of the promoters of SEQ ID NOs: 1 to SEQ ID NO: 5, four (Chos promoter, PK promoter, GK, and G6Pi promoter) were selected from the glycolysis metabolic pathway, and one (L-LDH promoter) was selected from the secondary metabolite lactate production pathway. These promoters are strong promoters that induce high-level expression of a heterologous nucleic acid in lactic acid bacteria (e.g., *Pediococcus pentosaceus*). These promoters enable the microorganism of the present invention to function as a drug delivery system and to produce and secrete a sufficient amount of a cystatin.

The gene construct may increase not only the expression level of a heterologous nucleic acid but also the secretion of the heterologous nucleic acid. As used herein, the expression "protein is secreted" means that the protein is transported extracellularly from microbial cells, and this expression includes the case in which the entire protein molecule is substantially present in medium in a completely released form, and also includes the case in which the entire protein molecule is present in the cell surface layer, and the case in which a portion of the protein molecule is present in medium while the remaining portion of the molecule is present in the cell surface layer.

The gene construct includes a secretion signal peptide in order to direct the exogenous protein, expressed by the microorganism, into the secretion pathway of the microbial cells. The secretion signal peptide sequence is usually located at the 5' end of the DNA sequence encoding the exogenous protein.

The gene construct may also include a replication origin replicable in microbial cells. The reason for this is that manipulation of the vector is more efficient in lactic acid bacteria strain, and preferred examples of the replication origin include ColE1, Ori, oriT, and the like.

The gene construct may include a secretion signal peptide sequence suitable for allowing the therapeutic peptide to be secreted or released from a microbial drug delivery system (e.g., a *Pediococcus pentosaceus* system). To allow secretion of the therapeutic peptide, a fragment encoding a secretion signal peptide suitable for use in *Pediococcus pentosaceus* may be added to the 5' end or 3' end of the heterologous nucleic acid sequence.

The secretion signal peptide may include a secretion signal peptide that directs strong protein secretion, such as a USP45 secretion signal, Usp45 N4 in which lysine at position 4 of a wild-type Usp45 secretion signal is substituted with asparagine, or a *Lactobacillus brevis* S-layer protein signal peptide. This secretion signal peptide is able to provide secretion of the exogenous protein of interest. In addition, this secretion signal peptide sequence can additionally control the production and secretion of the therapeutic polypeptide of interest.

In another embodiment of the present invention, the gene construct may further include, downstream of the promoter, a second promoter other than the above-described promoter of any one of SEQ ID NOs: 1 to 5, a second secretion signal peptide, and a second nucleic acid sequence encoding a biologically active polypeptide.

In another embodiment of the present invention, the gene construct may necessarily have a first promoter upstream of the heterologous nucleic acid to be expressed, and may also include a second promoter downstream of the heterologous nucleic acid to be expressed. The first promoter and the second promoter may be the same as or different from each other. It is possible to use not only a non-specific promoter capable of promoting the expression of a foreign gene in most cells or tissues, but also a specific or selective promoter, such as a tissue- or organ-specific promoter, a tumor-specific promoter, a development- or differentiation-specific promoter or the like. For example, a specific promoter may be used as the first promoter, and a non-specific promoter may be used as the second promoter. A microorganism transformed with a gene construct including these two promoters is capable of expressing a desired heterologous polypeptide or protein in a very high yield.

The microbial strain may be a strain belonging to the genus *Lactobacillus*, *Latococcus*, *Leuconostoc*, *Pediococcus*, or *Bifidobacterium*. Specific examples of the strain include, but are not necessarily limited to, *Lactobacillus rhamnosus*, *Lactobacillus acidophilus*, *Lactobacillus paracasei*, *Lactobacillus plantarum*, *Pediococcus pentosaceus*, or *Lactobacillus brevis* strains.

Preferably, the strain may be a *Pediococcus pentosaceus* strain. *Pediococcus pentosaceus* can survive during passage through the gastrointestinal tract due to its excellent acid resistance and bile juice resistance, and reach and adhere well to the intestinal mucosal layer in a living form, indicating that it can continuously function as a drug delivery system.

The strain that is used as a drug delivery system preferably *Pediococcus* PP CysA deposited under accession number KCCM12180P, but any strains for delivering a drug for treatment of gastrointestinal disease, which expresses and secretes the cystatin protein of the present invention, are all included in the scope of the present invention.

The microorganism of the present invention is obtained by transfecting a microbial strain with an expression vector including the gene construct, and thus a heterologous nucleic acid encoding a desired therapeutic peptide can be expressed by the microbial strain at a predetermined location in the gastrointestinal tract, thereby producing the therapeutic peptide.

Another aspect of the present invention is directed to a pharmaceutical composition for prevention or treatment of gastrointestinal disease, which includes the above-described microbial strain that produces and secretes a cystatin or an active fragment of the cystatin.

Still another aspect of the present invention is directed to a pharmaceutical composition for prevention or treatment of gastrointestinal disease, including a *Pediococcus pentosaceus* strain, wherein the *Pediococcus pentosaceus* strain includes a heterogeneous nucleic acid encoding a therapeutic peptide having a therapeutic effect against at least one gastrointestinal disease, wherein the heterogeneous nucleic acid includes: at least one promoter operably linked to the heterogeneous nucleic acid and selected from SEQ ID NOs: 1 to 5 and combinations thereof, derived from *Pediococcus pentosaceus*; and a gene encoding a secretion signal peptide.

The heterologous nucleic acid may preferably encode a therapeutic peptide or a disease-related polypeptide. In addition, the heterologous nucleic acid may encode an antigenic polypeptide for use as a vaccine. In the present invention, the heterologous nucleic acid may be a gene encoding a hormone, a cytokine, an enzyme, a coagulation factor, a transporter protein, a receptor, a regulatory protein, a structural protein, a transcription factor, an antigen, an antibody or the like. Specific examples thereof include, but are not limited to, genes encoding thrombopoietin, growth hormones, growth hormone-releasing hormones, growth hormone-releasing peptides, interferons, interferon receptors, colony-stimulating factors, glucagon-like peptides, G-protein coupled receptors, interleukins, interleukin receptors, enzymes, interleukin binding proteins, cytokine binding proteins, macrophage activators, macrophage peptides, B-cell factors, T-cell factors, protein A, allergy inhibitors, necrosis glycoproteins, immunotoxins, lymphotoxins, tumor necrosis factors, tumor suppressors, transforming growth factors, α-1 anti-trypsin, albumin, α-lactalbumin, apolipoprotein-E, erythropoietin, highly glycosylated erythropoietin, angiopoietin, hemoglobin, thrombin, thrombin receptor activating peptides, thrombomodulin, blood factors VII, VIIa, VIII, IX and XIII, plasminogen activators, fibrin-binding peptides, urokinases, streptokinases, hirudin, protein C, C-reactive proteins, superoxide dismutase, leptin, platelet-derived growth factors, epithelial growth factors, epidermal growth factors, angiostatin, angiotensin, bone growth factors, bone stimulating proteins, calcitonin, insulin, atriopeptin, cartilage inducing factors, elcatonin, connective tissue activating factors, follicle stimulating hormones, luteinizing hormones, luteinizing hormone releasing hormones, nerve growth factors, parathyroid hormones, relaxin, secretin, somatomedin, insulin-like growth factors, adrenocortical hormones, glucagon, cholecystokinin, pancreatic polypeptides, gastrin releasing peptides, corticotropin releasing factors, thyroid stimulating hormones, autotaxin, lactoferrin, myostatin, receptors, receptor antagonists, cell surface antigens, virus derived vaccine antigens, monoclonal antibodies, polyclonal antibodies, antibody fragments, and the like.

Gastrointestinal diseases suitable for treatment with the pharmaceutical composition of the present invention includes diseases and disorders that affect organs, such as the mouth, esophagus, stomach, small intestine, large intestine, rectum, pancreas, liver and gallbladder. For examples, the diseases include dry mouth, oral ulcer, gingival diseases, gastroesophageal reflux diseases, gastric ulcer, inflammatory bowel diseases, inflammatory colitis, Crohn's disease, mycositis, gastric cancer, and colorectal cancer. In particular, the pharmaceutical composition may advantageously be used for treatment of colorectal cancer, colitis, irritable bowel syndrome, and Crohn's disease.

The *Pediococcus pentosaceus* strain can survive during passage through the gastrointestinal tract due to its excellent acid resistance and bile juice resistance, and reach and adhere well to the intestinal mucosal layer in a living form, indicating that it can continuously function as a drug delivery system.

Still another aspect of the present invention is directed to a pharmaceutical composition for prevention or treatment of gastrointestinal disease, which includes the strain of the present invention, that is, a microorganism which has been transformed with a gene construct, including a polynucleotide encoding a cystatin or active fragment of the cystatin operably linked to an exogenous promoter and a gene encoding a secretion signal peptide, and which expresses and secretes the cystatin in the gastrointestinal tract.

The pharmaceutical composition of the present invention may further include a pharmaceutically acceptable carrier or pharmaceutically acceptable salt. Meanwhile, the pharmaceutical composition may further include a chemotherapeutic compound.

The composition of the present invention is preferably administered by a route that is most effective for treatment. The composition may be administered orally or by parenteral routes, such as intraoral, tracheobronchial, intrarectal, subcutaneous, intramuscular and intravenous routes. Dosage forms include sprays, capsules, tablets, granules, syrups, emulsions, suppositories, injections, ointments, tapes and the like.

For oral administration, gastroresistant oral dosage forms may be formulated, which may also include compounds providing controlled release of the host cells and thereby provide controlled release of the desired therapeutic peptide encoded therein. For example, the oral dosage form (including tablets, pellets, granulates, powders) may be coated with a thin layer of excipient (usually polymers, cellulosic derivatives and/or lipophilic materials) that resists dissolution or disruption in the stomach, but not in the intestine, thereby allowing transit through the stomach in favor of disintegration, dissolution and absorption in the intestine.

The oral dosage form may be designed to allow slow release of the host cells and of the recombinant protein thereof, for instance as controlled release, sustained release, prolonged release, sustained action tablets or capsules. These dosage forms usually contain conventional and well known excipients, such as lipophilic, polymeric, cellulosic, insoluble, swellable excipients. Controlled release formulations may also be used for any other delivery sites including intestinal, colon, bioadhesion or sublingual delivery (i.e., dental mucosal delivery) and bronchial delivery. Each of the aforementioned formulations are well known in the art.

Preparations suitable for oral administration include emulsions, syrups, capsules, tablets, powders, granules and the like. Liquid preparations such as emulsions or syrups may be prepared using, as additives, water, sugars such as sucrose, sorbitol and fructose, glycols such as polyethylene glycol and propylene glycol, oils such as sesame oil, olive oil and soybean oil, antiseptics such as p-hydroxybenzoates, flavors such as strawberry flavor and peppermint, and the like. Capsules, tablets, powders, granules, and the like may be prepared using, as additives, excipients such as lactose, glucose, sucrose and mannitol, disintegrating agents such as starch and sodium alginate, lubricants such as magnesium stearate and talc, binders such as polyvinyl alcohol, hydroxypropyl cellulose and gelatin, surfactants such as fatty acid esters, plasticizers such as glycerin, and the like.

Preparations suitable for parenteral administration include injections, suppositories, sprays and the like. Injections are prepared using carriers including a salt solution, a glucose solution, or a mixture thereof. Alternatively, powdery injections may also be prepared by freeze-drying the strain according to a conventional method and adding sodium chloride thereto. Suppositories are prepared using carriers such as cacao butter, hydrogenated fat or carboxylic acid. In addition, sprays are prepared using the compound itself and carriers which do not stimulate the oral and airway mucous membranes of a recipient and which disperse the compound into fine particles which are easily absorbed.

Specific examples of carriers include lactose, glycerin and the like. It is also possible to prepare aerosols, dry powders, and the like depending on the properties of the compound and the carriers used. For these parenteral preparations, the additive components described with respect to the oral preparations may also be added.

The dose of the therapeutic peptide-producing strain which is the active ingredient of the pharmaceutical composition according to the present invention may vary depending on the patient's age, sex, body weight and disease. However, the strain may be administered once or several times at a dose of 0.001 to 100 mg/kg, preferably 0.01 to 10 mg/kg.

In addition, the dose of the strain according to the present invention may be increased or decreased depending on the route of administration, the severity of the disease, the patient's sex, body weight, age and the like. Accordingly, the dose is not intended to limit the scope of the present invention in any way.

The present invention will be described in more detail below with reference to examples. However, these examples are for illustrative purposes only, and the scope of the present invention is not limited by these examples.

Examples

Example 1. Construction of System for Overexpression and Secretion of Lactic Acid Bacteria-Derived Protein Example 1-1. Selection of Promoters for Induction of Overexpression Five strong promoters (ChoS, L-carnitine, choline ABC transporter, permease protein; PK, pyruvate kinase; GK, glucokinase; G6Pi, glucose 6-phosphoate isomerase; and L-LDH, L-lactate dehydrogenase) for expression of a target protein (cystatin A) in lactic acid bacteria were selected from the glycolysis metabolic pathway. A host for expression of the target protein was *Pediococcus pentosaceus* SL4 (accession number: KCTC 10297BP). A previous experiment demonstrated that the glucose consumption rate of the host was very high, and HPLC analysis indicated that nearly 100% of the consumed glucose was converted to the secondary metabolite L-lactate. For this reason, of the promoters, four were selected from the glycolysis metabolic pathway, and one was selected from the secondary metabolite lactate production pathway.

Example 1-2. Construction of System for Overexpression and Secretion of Target Protein The plasmid pCBT24-2 (SEQ ID NO: 6) (KCCM12182P) was used for cloning of cystatin. The promoters selected in Example 1-1 were cloned with the DNA sequence encoding the usp45 secretion signal peptide [N-MKKKIISAILMST-VILSAAAPLSGVYA-C] derived from *Lactococcus lactis*, thereby constructing DNA plasmids in the form of promoter-secretion signal peptide-cystatin A (CysA). BamHI/PstI restriction enzyme sites were inserted into each promoter ligated with the secretion signal peptide. The constructed plasmids were as follows:
pCBT24-2-ChoS-usp45-CysA,
pCBT24-2-PK-usp45-CysA,
pCBT24-2-GK-usp45-CysA,
pCBT24-2-G6Pi-usp45-CysA, and
pCBT24-2-L-LDH-usp45-CysA.

Each of the plasmids was transformed into *Pediococcus pentosaceus* SL4 (accession number: KCTC 10297BP). The level of expression/secretion induced by each of the promoters was measured, and then promoters showing high activities were combined with each other, thereby constructing an expression vector (pCBT24-2-G6Pi-usp45-CysA-usp45-G6Pi-CysA), as shown in FIG. 2.

Figure 1:
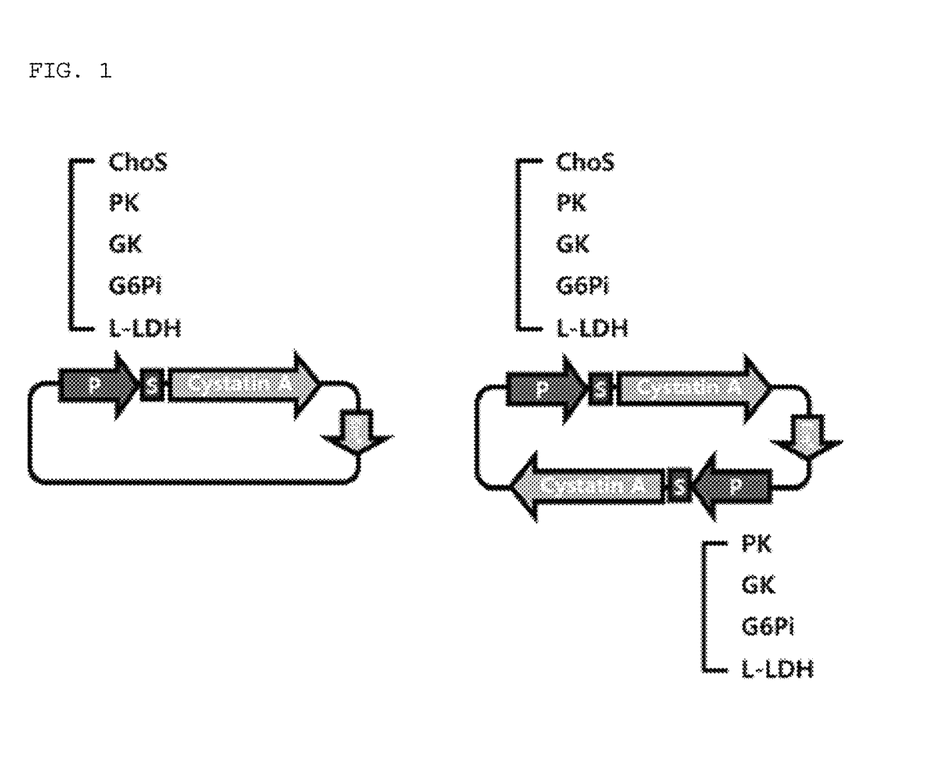
FIG. 1 is a view showing the configurations of expression vectors, including a single promoter and two promoters, respectively, used to transform a *Pediococcus pentosaceus* strain in an example of the present invention.
Figure 2:
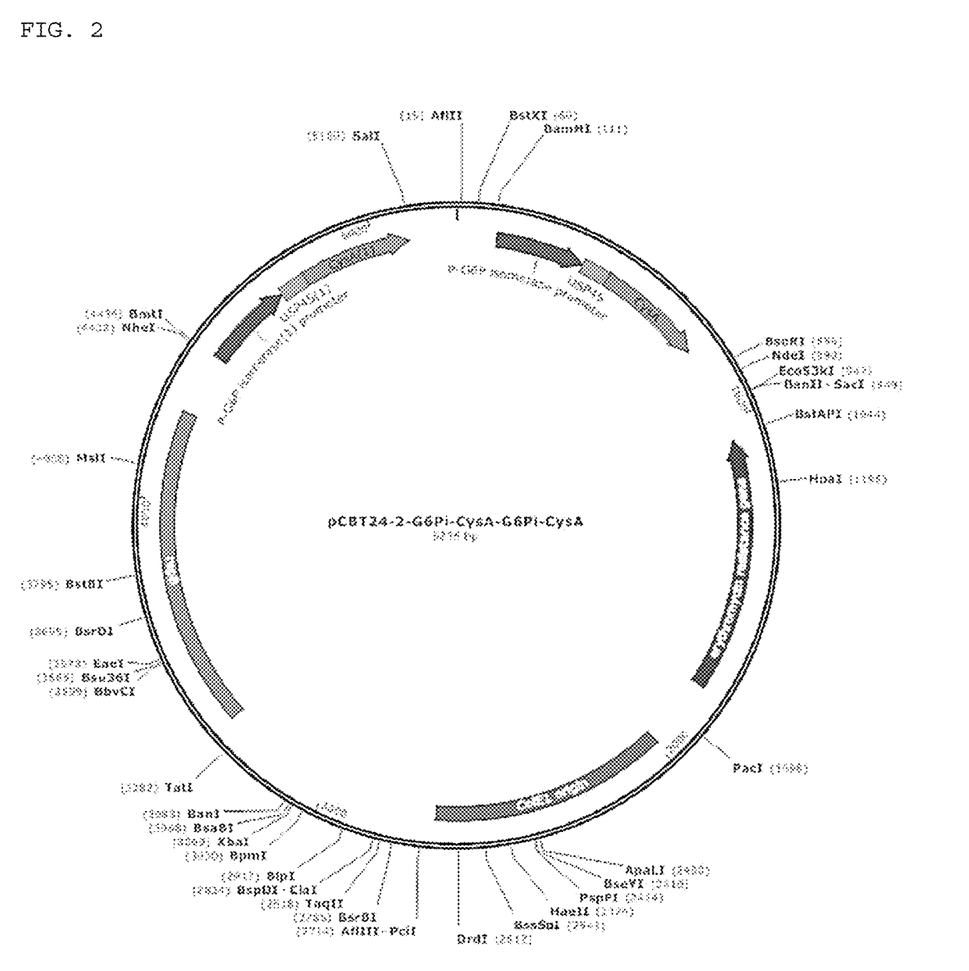
FIG. 2 is a cleavage map of an expression vector used to transform a *Pediococcus pentosaceus* strain in an example of the present invention.
Figure 3:
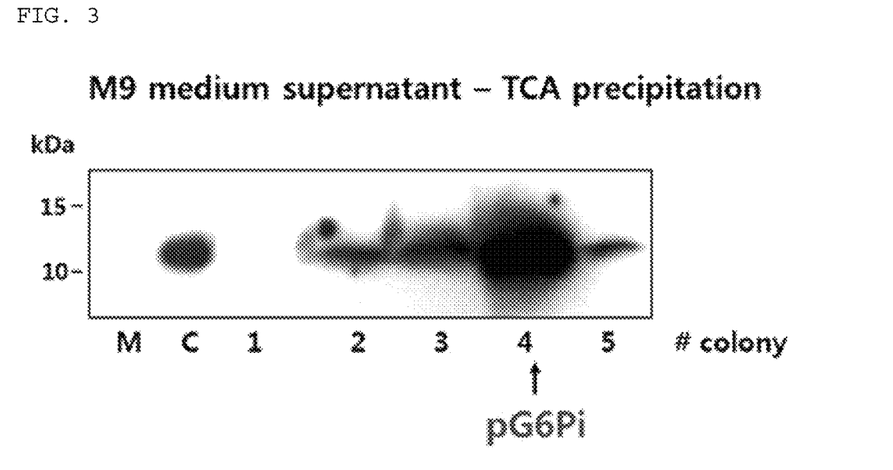
FIG. 3 is a photograph showing the results of Western blotting analysis performed to qualitatively analyze the expression level of cystatin A after the gene encoding cystatin A was cloned into a gene construct of the present invention.

The expression vector shown in FIG. 2 was transformed into *Pediococcus pentosaceus* SL4, and a transformant was selected. The transformant was mixed with LB liquid medium, and then cultured at 37° C. for 1 hour. The transformant cultured for 1 hour was plated onto LB agar medium containing erythromycin (final concentration: 10 μg/ml), and a strain showing resistance was first selected. The transformant was named PP CysA and deposited with the Korean Culture Center of Microorganisms (KCCM), located at Yurim B/D Hongjenae-2ga-gil, Seodaemun-gu, Seoul, Korea, on Nov. 30, 2017 under accession number KCCM12180P.

Example 1-3. Culture of *Pediococcus pentosaceus* SL4 Transformant

The transformant grown on MRS solid medium (agar plate) was inoculated into 10 ml of MRS liquid medium (containing 10 mg/ml of erythromycin) and statically cultured at 37° C. for 15 hours (overnight incubation). 1 ml of the culture was inoculated into 10 ml of M9 minimal medium (containing 10 mg/L of erythromycin), and then statically cultured at 37° C. for 48 hours. 5 ml of the culture was centrifuged, and the supernatant was collected. 5 ml of the supernatant was concentrated by TCA precipitation to isolate total protein. Using the total protein, the expression and secretion levels of cystatin A protein were comparatively analyzed by Western blotting. The microbial cells were diluted with buffer and lysed using a sonicator, and then the cell extract was analyzed by Western blotting, thereby determining the amount of cystatin A protein that was not secreted after expression.

Example 1-4. Isolation and Detection of Cystatin A Protein

The lactic acid bacteria transformant was cultured, and then 100% TCA (Trichloro Acetic Acid) was added to 5 ml of the culture supernatant to a final concentration of 20%. After mixing, the solution was incubated on ice for 30 minutes, and centrifuged at 15,000 rpm and 4° C. for 30 minutes to induce the precipitation of all proteins. After centrifugation, the supernatant was removed, and 200 µl of acetone was added to the precipitate which was then centrifuged at 15,000 rpm and 4° C., and the precipitated protein was washed. After the remaining acetone was completely removed by drying at room temperature, the secretion level of the target protein present in the culture supernatant was measured. The secretion level was measured by Western blotting, and the results of the measurement indicated that when the novel promoter was used, the expression/secretion levels significantly increased (see FIG. 4).

Example 2. Evaluation of Anticancer Effect of Cystatin Protein by Use of In Vivo Lactic Acid Bacteria Expression/Secretion System Example 2-1. Tumor Cell Transplantation and Tumor Transplantation The colorectal cancer cell line DLD-1 obtained from the Korean Cell Line Bank (Seoul, Korea) was subcultured at 37° C. in a 5% $CO_2$ incubator with RPMI 1640 medium (Sigma, MO, USA) containing 10% fetal bovine serum (FBS; Invitrogen, NY, USA), penicillin (0.02 UI/ml; Sigma, MO, USA), streptomycin (0.02 µg/ml; Sigma, MO, USA), glutamine (2 mM: Sigma, MO, USA) and non-essential amino acid (1%; Sigma, MO, USA). The cultured DLD-1 cells were suspended, and the tumor cell suspension were transplanted subcutaneously into the back of male nude mice (BALB/cAnN.Cg-Foxnlnu/CrlNarl; 5 weeks old) in an amount of 0.2 ml ($2 \times 10^6$ cells/mouse), thereby forming solid tumors. To dissect tumor tissue formed from the subcultured group, the animals were sacrificed and the tumor lumps were dissected. The blood vessels and fat layer distributed on the surface were removed, and then only fresh tumor tissue was selected and transplanted subcutaneously into untreated animals by a troca needle.

Example 2-2. Division into Experimental Groups and Substance Administration

When the volumes of individual tumors reached 100-150 $mm^3$ after transplantation of the tumor lumps, the body weights and the tumor sizes were measured, and the animals were randomly grouped. The experimental animals were divided into a total of seven groups as shown in Table 3 below, and each group consisted of 10 animals: a negative control group (tumor-transplanted control group: G1); a positive control group (a group administered with 5-Fu anticancer agent, 40 mg/Kg 5-Fu; 5-fluorouracil, Siyma, MO, USA: G2), and experimental groups {a group administered with $1 \times 10^9$ CFU/head after tumor cell transplantation (a group administered with wild-type *P. pentosaceus*), G3; a group administered with $1 \times 10^9$ CFU/head (a group administered with drug delivery system (DDS) *P. pentosaceus* (empty vector)): G4; a group administered with $1 \times 10^8$ CFU/head (a group administered with a low concentration of DDS *P. pentosaceus* (G6Pi-usp45-CysA): G5; a group administered with $1 \times 10^9$ CFU/head (a group administered with a middle concentration of DDS *P. pentosaceus* (G6Pi-usp45-CysA): G6; and a group administered with $1 \times 10^{10}$ CFU/head (a group administered with a high concentration of DDS *P. pentosaceus* (G6Pi-usp45-CysA): G7}. Each of the groups was administered orally with the indicated substance once a day for 7 weeks. Here, the transformant was cultured in MRS medium and suspended to a concentration of $10^{10}/200$ µl, and the suspension was administered orally once a day for a total of 6 weeks.

TABLE 3

Experimental groups and treatment items

| Group | Treatment | | Number of animals |
|---|---|---|---|
| G1 (NC1) | Treated with PBS | 100 µl/head | 10 |
| G2 (PC1) | 5-fluorouracil (5-Fu) | 400 µg/head | 10 |
| G3 (T1) | Wild-type | $1 \times 10^9$ CFU/head | 10 |
| G4 (T2) | Empty vector | $1 \times 10^9$ CFU/head | 10 |
| G5 (T3) | DDS PP (PK-usp45-CysA) low concentration | $1 \times 10^8$ CFU/head | 10 |
| G6 (T4) | DDS PP (PK-usp45-CysA) middle concentration | $1 \times 10^9$ CFU/head | 10 |
| G7 (T5) | DDS PP (PK-usp45-CysA) high concentration | $1 \times 10^{10}$ CFU/head | 10 |
| | Total number of animals | | 70 |

Example 2-3. Measurement of Change in Volume of Solid Cancer

The growth of tumors in the seven nude mouse groups (10 animals per group) transplanted with the colorectal cancer cell line DLD-1 was confirmed, and the tumor lumps transplanted subcutaneously into the right sides manifested as subcutaneous nodules 5 days after transplantation.

After tumor tissue transplantation, the animals were grouped as shown in Table 3 above, and were treated according to the dosage schedule. During the period from the 0th day before administration after tumor transplantation to 49th day after administration, the sizes of the tumor tissues were measured once a week with Vernier calipers. On the 49th day of the experiment, the xenograft models (solid cancer models) were sacrificed, and tissue samples were obtained, after which tumor metastasis was observed. The tumor volume was calculated using the following equation: $width^2 \times length/2$ ($mm^3$). The measured tumor sizes are graphically shown in FIGS. 4 and 5.

Figure 4:
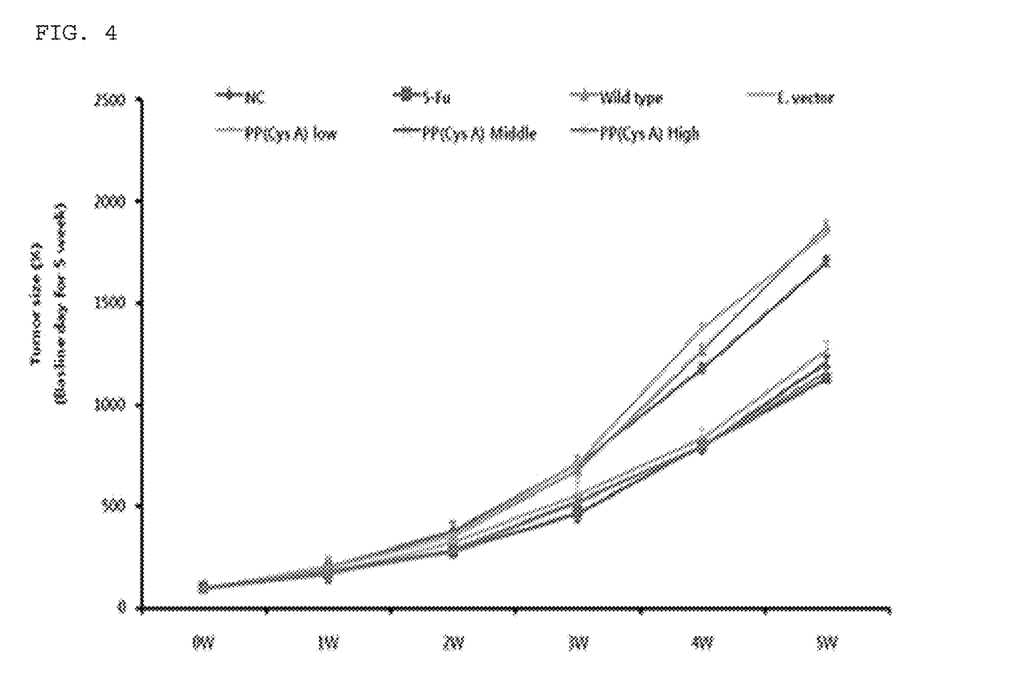
FIG. 4 is a graph comparing the tumor sizes after oral administration of microorganisms for delivery of a drug for treating gastrointestinal disease.
Figure 5:
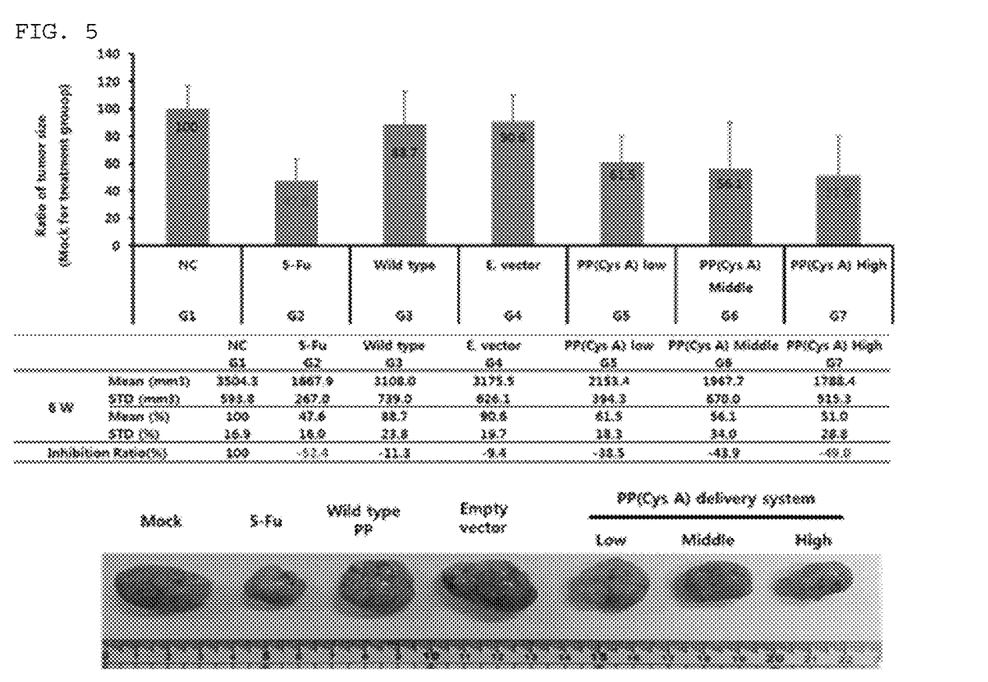
FIG. 5 shows a graph and a photograph including the anticancer activities after oral administration of microorganisms for delivery of a drug for treating gastrointestinal disease.

Referring to FIGS. 4 and 5, the results of verifying the effect of the cystatin A protein expressed and secreted from the drug delivery system (DDS) *Pediococcus pentosaceus* (G6Pi-usp45-CysA) indicated that the cystatin A protein inhibited cancer cell growth by 49.0% compared to that in the negative control group, and showed an anticancer activity of 93.5% compared to that shown in the positive control group. Referring to the photograph in the bottom of FIG. 5, it was confirmed that when the strain of the present invention was administered, the tumor size significantly decreased compared to those shown in the negative control group and the positive control group, and particularly in the case of the group administered with the high concentration of the strain, the tumor size was greatly reduced near the tumor size shown when 5-fluorouracil was administered, suggesting that the strain has excellent anticancer activity comparable to those of anticancer agents.

Although the preferred embodiments of the present invention have been described in detail, the present invention is not limited to the above-described embodiments. Those skilled in the art to which the present invention pertains will appreciate that various modifications and alterations may be easily made based on the above-described embodiments. Therefore, the true scope of protection of the present invention should be defined based on the appended claims and their equivalents.

The invention claimed is:

1. A *Pediococcus pentosaceus* strain for delivering a drug for treatment of colorectal cancer, comprising a gene construct that comprises:
 a polynucleotide encoding a cystatin or active fragment of the cystatin operably linked to an exogenous promoter; and
 a gene encoding a secretion signal peptide,
  wherein the gene construct expresses and secretes the cystatin or the active fragment of the cystatin in a gastrointestinal tract, and
  the exogenous promoter is at least one promoter selected from the group consisting of SEQ ID NO: 1 to SEQ ID NO: 5.

2. The microorganism of claim 1, wherein the secretion signal peptide is a USP45 secretion signal peptide, Usp45 N4 or a *Lactobacillus brevis* S-layer protein signal peptide.

3. The microorganism of claim 1, wherein the cystatin is selected from the group consisting of cystatin A, cystatin B, cystatin C, cystatin D, cystatin S, egg white cystatin, milk cystatin, and kininogen.

4. The microorganism of claim 1, wherein the gene construct further comprises, downstream of the promoter, a second promoter, a second secretion signal peptide and a second heterologous nucleic acid sequence, and the second promoter is identical to or different from the exogenous promoter.

* * * * *